(12) United States Patent
Katsurada et al.

(10) Patent No.: US 8,394,935 B2
(45) Date of Patent: Mar. 12, 2013

(54) METHOD FOR PRODUCING FURANOSE DERIVATIVE

(75) Inventors: Manabu Katsurada, Kanagawa (JP); Tomoko Sasaki, Tokyo (JP); Yasuko Nakajima, Tokyo (JP); Nobuo Kyoumura, Kanagawa (JP)

(73) Assignee: API Corporation, Osaka (JP)

( * ) Notice: Subject to any disclaimer, the term of this patent is extended or adjusted under 35 U.S.C. 154(b) by 646 days.

(21) Appl. No.: 12/517,900

(22) PCT Filed: Dec. 7, 2007

(86) PCT No.: PCT/JP2007/073663
§ 371 (c)(1),
(2), (4) Date: Sep. 17, 2009

(87) PCT Pub. No.: WO2008/069303
PCT Pub. Date: Jun. 12, 2008

(65) Prior Publication Data
US 2010/0105890 A1 Apr. 29, 2010

(30) Foreign Application Priority Data
Dec. 8, 2006 (JP) .................................. 2006-331755

(51) Int. Cl.
*C07H 1/00* (2006.01)
*C07H 1/06* (2006.01)
*C07H 3/02* (2006.01)
*C07H 15/04* (2006.01)

(52) U.S. Cl. ......................... 536/18.6; 536/124; 536/127

(58) Field of Classification Search .......................... None
See application file for complete search history.

(56) References Cited

U.S. PATENT DOCUMENTS
2002/0095033 A1 7/2002 Ramasamy et al.

FOREIGN PATENT DOCUMENTS
| JP | 9-508394 | 8/1997 |
| JP | 2003-176296 | 6/2003 |
| JP | 2005-539032 | 12/2005 |
| WO | WO 9520595 | 8/1995 |
| WO | WO 2004018492 | 3/2004 |

OTHER PUBLICATIONS

Cimpoia, A. R. et al., Journal of Carbohydrate Chemistry, "On the Conversion of Arabino- and Ribofuranosyl Methyl Glycosides to their 1-O-Acetyl Derivatives", 1994, vol. 13, No. 8, pp. 1115-1119.*
Erowid.org, "Molarity of Concentrated Reagents", also available at http://www.erowid.org/archive/rhodium/chemistry/equipment/molarity.html; last accessed Jul. 13, 2012.*
Shi, Z. -D. et al., A stereospecific synthesis of L-ribose and L-ribosides from D-galactose, Tetrahedron Letters, 2001, vol. 42, No. 43, pp. 7651-7653.
Wang, Guangyi et al., Synthesis and Cytokine Modulation Properties of Pyrrolo[2, 3-d]-4-pyrimidone Nucleosides, Journal of Medicinal Chemistry, 2000, vol. 43, No. 13, pp. 2566-2574.
Ramasamy, Kanda S. et al., Monocyclic L-Nucleosides with Type 1 Cytokine-Inducing Activity, Journal of Medicinal Chemistry, 2000, vol. 43, No. 5, pp. 1019-1028.
Recondo, E. F. et al., A new, simple, synthesis of 1-O-acetyl-2, 3, 5-trio-O-benzoyl-β-D-ribose, Helvetica Chimica Acta, 1959, vol. 42, pp. 1171 -1173.
Guthrie, R.D. et al., An improved preparation of 1,2,3,5-tetra-O-acetyl- β-D-ribofuranose, Chemistry & Industry, 1968, No. 17, pp. 547-548.
Zhang, Pingsheng et al., Synthesis of Methyl 1-(2,3,5-Tri-O-acetyl-β-L-ribofuranosyl) -1, 2,4-triazole-3-carboxylate from L-Ribose: From a Laboratory Procedure to a Manufacturing Process, Organic Process Research & Development, 2005, vol. 9, No. 5, pp. 583-592.
Sairam, Pothukuchi et al., Synthesis of 1,2,3-tri-O-acetyl-5-deoxy-D-ribofuranose from D-ribose, Carbohydrate Research, 2003, vol. 338, No. 4, pp. 303-306.
Witkowski, J. T. et al., Design, Synthesis, and Broad Spectrum Antiviral Activity of 1-β-D- Ribofuranosyl-1,2,4-triazole-3-carboxamide and Related Nucleosides, Journal of Medicinal Chemistry, 1972, vol. 15, No. 11, pp. 1150-1154.
Shimma, Nobuo et al., The Design and Synthesis of a New Tumor-Selective Fluoropyrimidine Carbamate, Capecitabine, Bioorganic & Medicinal Chemistry 8, 2000, pp. 1697-1706.
International Search Report and Written Opinion for International Patent Application No. PCT/JP2007/073663.

* cited by examiner

*Primary Examiner* — Shaojia Anna Jiang
*Assistant Examiner* — Bahar Craigo
(74) *Attorney, Agent, or Firm* — Greenblum & Bernstein, P.L.C.

(57) ABSTRACT

An object of the present invention is to provide a industrially appropriate method for producing the β-anomers of ribofuranose derivatives in a highly selective manner at a high yield. The present invention provides a method for producing ribofuranose derivatives wherein β-anomers is precipitated from among the generated furanose derivatives by controlling the amount of a reaction reagent used and/or using a poor solvent in the acetolysis reactions of 2,3,5-tri-O-acyl-1-O-alkyl-ribofuranose and 2,3-di-O-acyl-1-O-alkyl-5-deoxy-ribofuranose.

16 Claims, No Drawings

METHOD FOR PRODUCING FURANOSE DERIVATIVE

TECHNICAL FIELD

The present invention relates to a method for producing a furanose derivative, and specifically to a method for efficiently producing a furanose derivative, which comprises crystallizing β-anomer in a reaction system to increase the production amount of the β-anomer, in production of the α/β-mixtures of furanoses in which a hydroxyl group at anomeric position is acylated. A furanose derivative produced by the method of the present invention is useful as a synthetic intermediate of a nucleic acid derivative that is a pharmacologically active substance.

BACKGROUND ART

When sugars are used as medical or agrichemical intermediates and the like, they are produced in a stereoselective manner. In this case, from an industrial viewpoint, it is preferable to efficiently produce a stereoisomers of interest by suppressing generation of stereoisomers other than the original intention. In addition, it may be difficult to obtain a precursor of furanose and/or a furanose derivative, which is used as a starting material. Moreover, such material may be expensive. Thus, it is desirable to develop a method for industrially efficiently producing a furanose derivative having a stereoisomer of interest.

As disclosed in Patent Document 1, Non-Patent Documents 1, 2 and 3, and the like, a nucleic acid derivative obtained by condensing a furanose derivative having a specific configuration and a specific nitrogen-containing heterocyclic compound is extremely useful as a pharmacologically active substance which exhibits an antiviral action or an anticancer action. For example, 1-O-acetyl-2,3,5-tri-O-benzoyl-β-L-ribofuranose and 1,2,3,5-tetra-O-acetyl-β-L-ribofuranose can be converted to nucleic acid derivatives which are known to be useful as an antiviral agent, such as Clevudine (described in Patent Document 1) or L-Ribavirin (Levovirin) (described in Non-Patent Document 2). Moreover, 1,2,3-tri-O-acetyl-5-deoxy-β-D-ribofuranose can be converted to Capecitabine (described in Non-Patent Document 3), for example.

As a furanose derivative to be condensed with a nitrogen-containing heterocyclic compound, there is generally used a furanose derivative in which hydroxyl groups at 1-, 2-, 3- and 5-positions are protected, or a 5-deoxyribofuranose derivative in which hydroxyl groups at 1-, 2- and 3-positions are protected. As such protecting group, an acyl group is generally used because of the easiness of introduction or removal thereof.

For instance, the nucleic acid derivatives exhibiting pharmacological activity disclosed in Patent Document 1 and Non-Patent Documents 2 and 3 are all β-anomers, if the anomeric position of the furanose site thereof is focused. As furanose derivatives used in production of such nucleic acid derivatives, β-anomers are used.

The most commonly used method for synthesizing 1-O-acetyl-2,3,5-tri-O-benzoyl-β-L-ribofuranose (hereinafter referred to as "β-L-ATBR" at times) that is an example of the furanose derivative of interest of the present invention is a method of converting 2,3,5-tri-O-benzoyl-1-O-methyl-L-ribofuranose (hereinafter referred to as "L-TBM" at times) to β-L-ATBR using acetic anhydride (6.0 equivalents), acetic acid (4.2 equivalents), and sulfuric acid (3 equivalents), which is described in Non-Patent Document 4. However, this method has been problematic in that an α-anomer as a stereoisomer at 1-position of L-ATBR is generated with respect to a β-anomer at a ratio of β/α=65/35, and in that the yield of the β-anomer (β-L-ATBR) is decreased. Moreover, a crude crystal of β-L-ATBR containing a large amount of such α-anomer has crystal properties that are poorer than those of high-purity crude crystal of β-L-ATBR. Thus, when a filtration operation is carried out to produce such crude crystal, filtration ability is poor, and it takes a long period of time to carry out such filtration operation. Hence, production of such crude crystal of β-L-ATBR has been problematic. Furthermore, an excessive amount (6 equivalents) of acetic anhydride is used in this reaction. When this reaction is terminated, the reaction must be terminated by addition of water. However, a large amount of acetic anhydride remains in this method, and thus this method generates a large calorific power. Accordingly, after completion of the reaction, the reaction solution must be slowly added dropwise into water that has been cooled in another vessel, and thus two different reactors are necessary for this reaction. Hence, this method has been industrially problematic.

Methods for producing 1,2,3,5-tetra-O-acetyl-ribofuranose are disclosed in Patent Document 2, and Non-Patent Documents 2, 5 and 6.

In known methods, D- or L-ribose is allowed to react with lower alkanol in the presence of strong acid so as to alkylate the hydroxyl group at 1-position, and the obtained acetal is then treated with acetic anhydride in an acetic acid solvent or in the presence of a base so as to acetylate the hydroxyl groups at 2-, 3- and 5-positions. The subsequent acetolysis is carried out in acetic acid and acetic anhydride in the presence of strong acid.

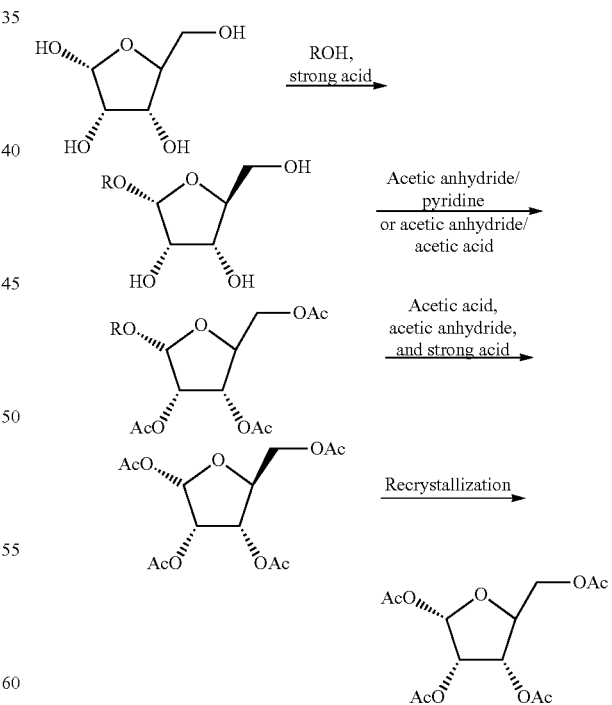

In Non-Patent Document 5, D-ribose is used as a starting material, the alkylation of the hydroxyl group at 1-position is carried out in methanol in the presence of sulfuric acid, the acetylation is carried out with acetic anhydride in pyridine, and the acetolysis is carried out in acetic acid and acetic anhydride in the presence of concentrated sulfuric acid. By recrystallizing from ethanol, 1,2,3,5-tetra-O-acetyl-β-D-ribofuranose is obtained at a total yield of 55%. Moreover, the hydroxyl group at 1-position is methylated, and thereafter, acetylation and the subsequent acetolysis are carried out in acetic acid and acetic anhydride in the presence of concentrated sulfuric acid. Thereafter, by recrystallizing from ethanol, 1,2,3,5-tetra-O-acetyl-β-D-ribofuranose is obtained at a total yield of 53%.

In Non-Patent Document 2, L-ribose is used as a starting material, the alkylation of the hydroxyl group at 1-position is carried out in methanol that contains hydrochloric acid, the acetylation is carried out with acetic anhydride in pyridine, and the acetolysis is carried out in acetic acid and acetic anhydride in the presence of concentrated sulfuric acid. By recrystallizing from ethyl ether, 1,2,3,5-tetra-O-acetyl-β-L-ribofuranose is obtained at a total yield of 57%. Hereinafter, in the present specification, 1,2,3,5-tetra-O-acetyl-β-L-ribofuranose may be referred to as β-L-TAR at times, and 1,2,3,5-tetra-O-acetyl-L-ribofuranose may be referred to as L-TAR at times.

In Non-Patent Document 6, L-ribose is used as a starting material, the methylation of the hydroxyl group at 1-position is carried out in methanol in the presence of sulfuric acid, the resultant mixture is then treated with lithium carbonate, the acetylation is then carried out in acetic acid and acetic anhydride, and concentrated sulfuric acid and acetic anhydride are further added thereto to carry out the acetolysis. A crude product is a mixture of α/β-anomers of 1,2,3,5-tetra-O-acetyl-L-ribofuranose. The crude product is treated with water and isopropyl alcohol to obtain 1,2,3,5-tetra-O-acetyl-β-L-ribofuranose at a total yield of 60%.

Herein, with regard to 1,2,3,5-tetra-O-acetyl-ribofuranose, for example, its β-anomer is a solid, and its α-anomer is an oily substance. In order to separate the product of interest from by-products generated in the process of converting ribose to the product of interest and to purify the product of interest, β-anomer that can be recrystallized from an inexpensive solvent or can be purified by washing is advantageous in terms of industrial production.

A ribofuranose having a specific configuration is extremely expensive. Thus, it is desired to convert ribofuranose to a ribofuranose derivative of interest whose hydroxyl groups at 1-, 2-, 3- and 5-positions are protected by acryl groups at a high yield. In the case of prior art techniques, when L-ribofuranose is converted to 1,2,3,5-tetra-O-acetyl-β-L-ribofuranose, for example, the total yield is only 60%. The biggest reason for the considerable low yield of the β-anomer (β-L-TAR) is considered to be generation of α-anomer as well as the β-anomer of interest. The ratio of the two types of anomers generated is β/α=approximately 3/1. Non-Patent Document 6 discloses that such ratio can be improved to β/α=approximately 5/1 by altering the reaction conditions for acetolysis. However, this document describes that the sum of the acetolysis products, namely, the yield of L-TAR including both α- and β-anomers, is decreased under reaction conditions in which the ratio of the two types of anomers generated has been improved to β/α=approximately 5/1. As a result, the yield of isolable β-L-TAR is hardly improved. Thus, it cannot be said that these known methods are sufficient for industrial, efficient and inexpensive production of β-anomer that is useful as an intermediate for production of nucleic acid derivatives.

Moreover, a method for synthesizing 1,2,3-tri-O-acetyl-5-deoxy-β-D-ribofuranose (hereinafter referred to as "β-D-DTAR" at times in the present specification) is described in Non-Patent Document 7. That is, 1-O-methyl-5-deoxy-D-ribofuranose is induced via 3 steps from a D-ribofuranose derivative in which the hydroxyl groups at 2- and 3-positions of 1-O-methyl-D-ribofuranose are protected by acetonide. Thereafter, the acetylation of the hydroxyl groups at 2- and 3-positions of the 1-O-methyl-5-deoxy-D-ribofuranose is carried out with acetic anhydride in pyridine. The acetolysis of the obtained 2,3-di-O-acetyl-1-O-methyl-5-deoxy-D-ribofuranose is carried out in acetic acid and acetic anhydride in the presence of concentrated sulfuric acid, so as to convert the compound to 1,2,3-tri-O-acetyl-5-deoxy-β-D-ribofuranose (hereinafter referred to as "D-DTAR" at times in the present specification). With regard to D-DTAR, its β-anomer is a solid, and its α-anomer is an oily substance. Thus, in order to separate the product of interest from by-products generated in the process of converting ribose to the product of interest and to purify the product of interest, β-anomer that can be recrystallized from an inexpensive solvent or can be purified by washing is industrially advantageous. However, the anomer ratio of the obtained crude D-DTAR is β/α=3/1. Thus, this has not been a method for efficiently obtaining the β-anomer of interest.

Patent Document 1: JP Patent Publication (Kohyo) No. 9-508394 A (1997)
Patent Document 2: JP Patent Publication (Kohyo) No. 2005-539032 A
Non-Patent Document 1: J. Med. Chem., 11: 1150 (1972)
Non-Patent Document 2: J. Med. Chem., 43: 1019 (2000)
Non-Patent Document 3: Bioorganic & Medicinal Chemistry, 1697 (2000)
Non-Patent Document 4: Helvetica Chimica Acta 1959 (121) 1171-1173
Non-Patent Document 5: Chem. Ind., 547 (1968)
Non-Patent Document 6: Org. Proc. Res. Develop., 9: 583 (2005)
Non-Patent Document 7: J. Med. Chem., 43: 2566 (2000)

DISCLOSURE OF THE INVENTION

Problem to be Solved by the Invention

As mentioned above, a method for industrially and inexpensively producing the β-anomer of a ribofuranose derivative whose hydroxyl groups at 1-, 2-, 3- and 5-positions are protected by protecting groups such as an acyl group and/or the β-anomer of a 5-deoxyribofuranose derivative whose hydroxyl groups at 1-, 2- and 3-positions are protected by protecting groups such as an acyl group in a highly selective manner at a high yield has not yet been known. Thus, it has been desired to discover such method. That is to say, an object of the present invention is to provide a industrially appropriate method for producing the β-anomers of ribofuranose derivatives such as β-L-ATBR, β-L-TAR and β-D-DTAR in a highly selective manner at a high yield.

Means for Solving the Problem

As a result of intensive studies directed towards achieving the aforementioned object, the present inventors have discovered a method for producing β-anomers in a highly selective manner at a high yield, which is applied when ribose is converted to 1-O-acetyl-2,3,5-tri-O-acyl-ribofuranose such as 1-O-acetyl-2,3,5-tri-O-benzoyl-β-L-ribofuranose or 1,2,3,5-tetra-O-acetyl-β-L-ribofuranose, and when ribose is converted to 1-O-acetyl-2,3-di-O-acyl-5-deoxy-ribofuranose such as 1,2,3-tri-O-acetyl-5-deoxy-β-D-ribofuranose. That is, the present invention relates to a method for producing ribofuranose derivatives wherein β-anomers is precipitated from among the generated furanose derivatives by controlling the amount of a reaction reagent used and/or using a poor solvent in the acetolysis reactions of 2,3,5-tri-O-acyl-1-O-alkyl-ribofuranose and 2,3-di-O-acyl-1-O-alkyl-5-deoxy-ribofuranose.

According to the present invention, the following invention is provided.

(1) A method for producing a compound represented by the following formula (4):

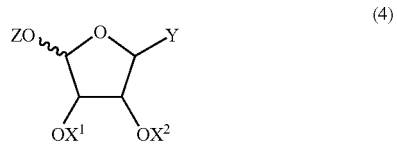

(4)

wherein each of $X^1$ and $X^2$ represents a protecting group of a hydroxyl group, which may be the same or different, Y represents $CH_2OX^3$ or $CH_3$; $X^3$ represents a protecting group of a hydroxyl group; and Z represents an acyl group, which comprises allowing an acylating agent to react with a compound represented by the following formula (3) in the presence of acid:

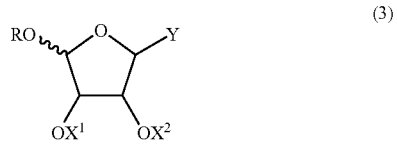

(3)

wherein each of $X^1$ and $X^2$ represents a protecting group of a hydroxyl group, which may be the same or different; Y represents $CH_2OX^3$ or $CH_3$; $X^3$ represents a protecting group of a hydroxyl group; and R represents a lower alkyl group, wherein conditions for the reaction of allowing the acylating agent to react with the compound represented by formula (3) are determined in such a way that the produced compound represented by formula (4) whose configuration at 1-position is β (β-anomer) is precipitated.

(2) The method according to (1) above, wherein the condition is determined in such a way that the ratio of the α-anomer/β-anomer (α-anomer:β-anomer) as to the configuration at 1-position of the generated compound of formula (4) is 30:70 to 0:100.

(3) The method according to (1) or (2) above, wherein the compound of formula (4) whose configuration at 1-position is β-anomer is precipitated by controlling the amount of the acylating agent used and/or by using a poor solvent (4) The method according to any one of (1) to (3) above, wherein the acid is strong acid.

(5) The method according to (4) above, wherein the acid is sulfuric acid.

(6) The method according to any one of (1) to (5) above, which further comprises adding a base.

(7) The method according to (6) above, wherein the base is an organic base.

(8) The method according to any one of (1) to (7) above, wherein the acylating agent is acetic acid, acetic anhydride, or a mixture thereof.

(9) The method according to (8) above, wherein the amount of the acetic anhydride used is 3 equivalents or less with respect to the amount of the compound of formula (3) used, or the amount of the acetic acid used is 5 equivalents or less with respect to the amount of the compound of formula (3) used.

(10) The method according to (3) above, wherein the poor solvent is any one of an ether solvent, an aliphatic hydrocarbon solvent, and an aromatic hydrocarbon solvent.

(11) The method according to any one of (1) to (10) above, wherein the compound of formula (3) is used, which is obtained by allowing a compound represented by the following formula (1) to react with lower alcohol in the presence of acid:

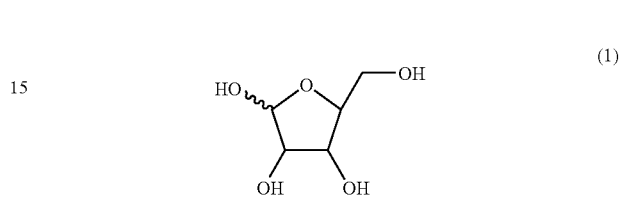

(1)

so as to produce a compound represented by the following formula (2):

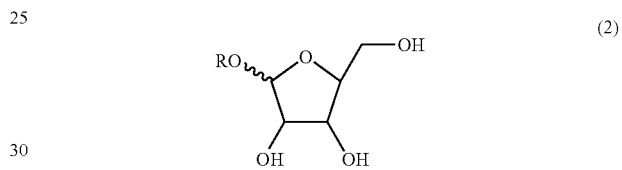

(2)

wherein R represents a lower alkyl group, and then allowing a compound represented by X—Cl or $X_2O$ wherein X represents a protecting group of a hydroxyl group, to act on the thus produced compound of formula (2) to obtain the compound of formula (3).

(12) The method according to any one of (1) to (11) above, which comprises isolating the β-anomer of the produced compound of formula (4) by further crystallizing the compound of formula (4).

(13) The method according to any one of (1) to (12) above, which further comprises converting a group represented by —OZ at 1-position of the produced compound of formula (4) to another group.

Effect of the Invention

The present invention relates to a method for producing ribose derivatives such as L-ATBR, L-TAR and D-DTAR. According to the present invention, the β-anomers of such furanose derivatives useful as pharmaceutical intermediates can be obtained in a highly selective manner at a high yield by an industrially appropriate method.

L-ATBR and L-TAR that are ribose derivatives obtained by the method of the present invention can be converted to nucleic acid derivatives that are known to be useful as an antiviral agent, such as Levovirin described in JP Patent Publication (Kohyo) No. 2005-539032 and Clevudine described in JP Patent Publication (Kohyo) No. 9-508394 A (1997). Moreover, D-DTAR can be converted to nucleic acid derivatives that are known to be useful as an anticancer agent, such as Capecitabine described in Bioorganic & Medicinal Chemistry, 2000, 1967. Thus, these are all compounds useful as pharmaceutical or agrochemical intermediates.

BEST MODE FOR CARRYING OUT THE INVENTION

Hereafter, the embodiments of the present invention will be described in detail.

The method of the present invention relates to a method for producing a compound represented by the formula (4) defined in the present specification which comprises allowing an acylating agent to react with a compound represented by the formula (3) defined in the present specification in the presence of acid, wherein conditions for the reaction of allowing the acylating agent to react with the compound represented by formula (3) are determined in such a way that β-anomer can be precipitated from the generated compound of formula (4). In a preferred embodiment of the present invention, β-anomer can be precipitated from the generated compound of formula (4) by controlling the amount of the acylating agent used and/or by using a poor solvent.

In the compounds of formulae (1) to (4) defined in the present specification, the configuration of positions (namely, 2-, 3- and 4-positions) other than 1-position (the position indicated with a wavy line, namely, an anomeric position) is not particularly limited. In addition, the sugar used in the present invention may be either a D-form or an L-form.

In the present invention, the configuration of 1-position of the compound of formula (4) can be determined, so that the ratio of α-/β-anomers generated (α-anomer:β-anomer) can become preferably from 30:70 to 0:100, more preferably from 20:80 to 0:100, further preferably from 15:85 to 0:100, and particularly preferably from 10:90 to 0:100. More specifically, when 1-O-acetyl-2,3,5-tetra-O-benzoyl-β-ribofuranose is synthesized, the aforementioned configuration can be determined, so that the ratio of α-/β-anomers generated (α:β) can become preferably from 30:70 to 0:100, more preferably from 20:80 to 0:100, further preferably from 15:85 to 0:100, and particularly preferably from 10:90 to 0:100. Moreover, when 1,2,3,5-tetra-O-acetyl-β-ribofuranose is synthesized, the aforementioned configuration can be determined, so that the ratio of α-/β-anomers generated (α-anomer:β-anomer) can become preferably from 30:70 to 0:100, more preferably from 20:80 to 0:100, further preferably from 15:85 to 0:100, and particularly preferably from 10:90 to 0:100. Furthermore, when 1,2,3-tri-O-acetyl-5-deoxy-β-ribofuranose is synthesized, the aforementioned configuration can be determined, so that the ratio of α-/β-anomers generated (α-anomer:β-anomer) can become preferably from 30:70 to 0:100, more preferably from 20:80 to 0:100, further preferably from 15:85 to 0:100, and particularly preferably from 10:90 to 0:100.

In the present invention, each of $X^1$ and $X^2$ represents a protecting group of a hydroxyl group, which may be the same or different. Examples of such hydroxyl-protecting groups used in the present invention include protecting groups that are commonly used in the field of organic chemical synthesis. Specific examples include the following groups.

(Ether-Type Groups)
methyl group, methoxymethyl group, methylthiomethyl group, benzyloxymethyl group, t-butoxymethyl group, 2-methoxyethoxymethyl group, 2,2,2-trichloroethoxymethyl group, bis(2-chloroethoxy)methyl group, 2-(trimethylsilyl)ethoxymethyl group, tetrahydropyranyl group, 3-bromotetrahydropyranyl group, tetrahydrothiopyranyl group, 4-methoxytetrahydropyranyl group, 4-methoxytetrahydrothiopyranyl group, 4-methoxytetrahydrothiopyranyl S,S-dioxide group, tetrahydrofuranyl group, tetrahydrothiofuranyl group, triisopropylsilyloxymethyl group (TOM) group); 1-ethoxyethyl group, 1-methyl-1-methoxyethyl group, 1-(isopropoxy)ethyl group, 2,2,2-trichloroethyl group, 2-(phenylselenyl)ethyl group, t-butyl group, allyl group, cinnamyl group, p-chlorophenyl group, benzyl group, p-methoxybenzyl group, o-nitrobenzyl group, p-nitrobenzyl group, p-halobenzyl group, p-cyanobenzyl group, 3-methyl-2-picolyl N-oxide group, diphenylmethyl group, 5-dibenzosuberyl group, triphenylmethyl group, α-naphthyldiphenylmethyl group, p-methoxyphenyldiphenylmethyl group, p-(p'-Bromophenacyloxy)phenyldiphenylmethyl group, 9-anthryl group, 9-(9-phenyl)xanthenyl group, 9-(9-phenyl-10-oxo)anthryl group, benzisothiazolyl S,S-dioxide group; trimethylsilyl group, triethylsilyl group, isopropyldimethylsilyl group, t-butyldimethylsilyl group (TBDMS group), (triphenylmethyl)dimethylsilyl group, t-butyldiphenylsilyl group, methyldiisopropylsilyl group, methyl-di-t-butylsilyl group, tribenzylsilyl group, tri-p-xylylsilyl group, triisopropylsilyl group, triphenylsilyl group;

(Ester-Type Groups)
formyl group, benzoylformyl group, acetyl group, chloroacetyl group, dichloroacetyl group, trichloroacetyl group, trifluoroacetyl group, methoxyacetyl group, triphenylmethoxyacetyl group, phenoxyacetyl group, p-chlorophenoxyacetyl group, 2,6-dichloro-4-methoxyphenoxyacetyl group, 2,6-dichloro-4-(1,1,3,3-tetramethylbutyl)phenoxyacetyl group, 2,4-bis(1,1-dimethylpropyl)phenoxyacetyl group, chlorodiphenylacetyl group, p-P-phenylacetyl group, 3-phenylpropionyl group, 3-benzoylpropionyl group, isobutyryl group, monosuccinyl group, 4-oxopentanoyl group, pivaloyl group, adamantoyl group, crotonyl group, 4-methoxycrotonyl group, (E)-2-methyl-2-butenoyl group, benzoyl group, o-(dibromomethyl)benzoyl group, o-(methoxycarbonyl)benzoyl group, p-phenylbenzoyl group, 2,4,6-trimethylbenzoyl group, p-P-benzoyl group, α-naphthoyl group;

(Carbonate-Type Groups)
methoxycarbonyl group, ethoxycarbonyl group, 2,2,2-trichloroethoxycarbonyl group, isobutoxycarbonyl group, vinyloxycarbonyl group, allyloxycarbonyl group, cinnamyloxycarbonyl group, p-nitrophenyloxycarbonyl group, benzyloxycarbonyl group, p-methoxybenzyloxycarbonyl group, 3,4-dimethoxybenzyloxycarbonyl group, o-nitrobenzyloxycarbonyl group, p-nitrobenzyloxycarbonyl group, S-benzylthiooxycarbonyl group;

(Other Groups)
N-phenylcarbamyl group, N-imidazolylcarbamyl group, boryl group, nitrile group, N,N,N',N'-tetramethylphosphorodiamidyl group, 2,4-dinitrophenylsulfenyl group.

Methods of introducing and deprotecting the aforementioned protecting group of a hydroxyl group are well known to persons skilled in the art. Such method is described, for example, in Protective Groups in Organic Synthesis, John & Wiley & Sons Inc. (1981) and the like.

In the present invention, Y represents $CH_2OX^3$ or $CH_3$, and $X^3$ represents a protecting group of a hydroxyl group. Specific examples of the protecting group of a hydroxyl group represented by $X^3$ include those represented by $X^1$ and $X^2$ above in the present specification. The protecting group of a hydroxyl group represented by $X^3$ may be identical to or different from those represented by $X^1$ and $X^2$.

In the present invention, R represents a lower alkyl group. The lower alkyl group is preferably a linear, branched or cyclic alkyl group containing 1 to 10 carbon atoms, more preferably a linear or branched alkyl group containing 1 to 6 carbon atoms, and further preferably a linear or branched alkyl group containing 1 to 4 carbon atoms. Examples of the lower alkyl group include a methyl group, an ethyl group, an isopropyl group, a normal propyl group, a normal butyl group, and a t-butyl group. The most preferable example is a methyl group.

In the present invention, Z represents an acyl group. The acyl group may be either an aliphatic acyl group or an aromatic acyl group. Examples thereof include an acyl group containing 2 to 7 carbon atoms. Examples of the acyl group include an acetyl group, a propionyl group, a butyryl group, a pentanoyl group, a hexanoyl group, a heptanoyl group, an isobutyryl group, a pivaloyl group, a cyclohexanecarbonyl group, and a benzoyl group. A particularly preferred example is an acetyl group.

The acylating agent used in the present invention is not particularly limited, as long as it acts on the compound of formula (3) in the presence of acid to produce the compound of formula (4). It is preferably an acid halide or an acid anhydride. The type of acid halide or acid anhydride is not particularly limited. Specific examples of acid halide include: acid chlorides such as acetyl chloride, isobutyric acid chloride, pivaloyl chloride, cyclohexanecarbonyl chloride, benzoyl chloride, and 4-methoxybenzoyl chloride; acid bromides such as acetyl bromide, isopropionic acid bromide, pivaloyl bromide, cyclohexanecarbonyl bromide, benzoyl bromide, and 4-methoxybenzoyl bromide; and acid iodides such as acetyl iodide, isobutyric acid iodide, pivaloyl iodide, cyclohexanecarbonyl iodide, benzoyl iodide, and 4-methoxybenzoyl iodide. Specific examples of such acid anhydride include acetic anhydride, propionic anhydride, pivalic anhydride, cyclohexanecarboxylic anhydride, and benzoic anhydride. Of these, acetic anhydride is preferable. In addition, acetic acid can be used as an acylating agent. Particularly preferred acylating agents used in the present invention include acetic acid, acetic anhydride, and a mixture thereof.

The amount of the acylating agent used is preferably determined, so that β-anomer can be precipitated from the compound of formula (4) produced by the method of the present invention. For example, the amount of the acylating agent used is preferably 6 equivalents or less, and more preferably 4 equivalents or less, with respect to the amount of the compound of formula (3) used. When a combination of acetic anhydride and acetic acid is used as an acylating agent, for example, the amount of the acetic anhydride used is preferably 3 equivalents or less with respect to the amount of the compound of formula (3) used, and the amount of acetic acid used is preferably 5 equivalents or less with respect to the amount of the compound of formula (3) used. When only acetic anhydride is used as an acylating agent, the amount of acetic anhydride used is preferably 3 equivalents or less with respect to the amount of the compound of formula (3) used.

In the present invention, an acylating agent is allowed to act on the compound of formula (3) in the presence of acid. The acid used in the present invention may be either weak acid or strong acid. Strong acid is preferable. Moreover, the acid may be either inorganic acid (for example, sulfuric acid, hydrochloric acid, nitric acid, etc.) or organic acid (formic acid, benzoic acid, methanesulfonic acid, trifluoromethanesulfonic acid, p-toluenesulfonic acid, etc.). Inorganic acid is preferable. As such acid, sulfuric acid or hydrochloric acid is particularly preferably used.

The amount of acid used is not particularly limited, as long as the compound of formula (4) can be produced by allowing an acylating agent to act on the compound of formula (3) in the presence of such acid. For example, the amount of the acid used is preferably 5 equivalents or less, and more preferably 3 equivalents or less, with respect to the amount of the compound of formula (3) used.

In the present invention, when an acylating agent is allowed to act on the compound of formula (3) in the presence of acid, a base may be further added. The base may be either an organic base (for example, tertiary amines such as trimethylamine, triethylamine, diisopropylethylamine and tri-normal propylamine, pyridine, etc.) or an inorganic base (for example, potassium hydroxide, sodium hydroxide, etc.). An organic base is preferable. Pyridine is particularly preferably used as such a base.

The amount of such a base used is not particularly limited, as long as the compound of formula (4) can be produced by allowing an acylating agent to act on the compound of formula (3) in the presence of such a base. For example, the amount of the base used is preferably 3 equivalents or less, and more preferably 1 equivalent or less, with respect to the amount of the compound of formula (3) used.

In the present invention, when an acylating agent is allowed to act on the compound of formula (3) in the presence of acid, a poor solvent may be further added. In the present invention, using such a poor solvent, β-anomer may be precipitated from the compound of formula (4) generated. The poor solvent may be present in the reaction system from the beginning of the reaction, or it may also be added during the reaction. Moreover, such a poor solvent may also be added before termination of the reaction, so as to precipitate β-anomer. The poor solvent that can be used in the present invention is a solvent in which the solubility of the compound of formula (3) is low. For example, in the present invention, a solvent in which the solubility of the compound of formula (3) is preferably 200 g/L or less, and more preferably 20 g/L or less, can be used as a poor solvent.

The poor solvent used in the present invention is preferably any one of an ether solvent, an aliphatic hydrocarbon solvent, and an aromatic hydrocarbon solvent. Examples of ether solvent include diethyl ether, diisopropyl ether, di-normal propyl ether, di-normal butyl ether, methyl isopropyl ether, methyl-t-butyl ether, ethyl-t-butyl ether, tetrahydrofuran, and dioxane. Examples of aliphatic hydrocarbon solvent include hexane and heptane. Examples of aromatic hydrocarbon solvent include toluene and xylene. The aforementioned ether solvents are preferable, but examples are not limited thereto. The poor solvent may be used singly, or as a mixed solvent consisting of several types of solvents.

The amount of a poor solvent used is not particularly limited, as long as the compound of formula (4) can be produced by allowing an acylating agent to act on the compound of formula (3) in the presence of such a poor solvent. For example, the amount of such a poor solvent used is preferably 20 times or less, and more preferably 10 times or less, with respect to the amount of the compound of formula (3).

A reaction temperature applied when the compound of formula (4) is produced by allowing an acylating agent to act on the compound of formula (3) in the presence of acid is not particularly limited. A temperature, at which β-anomer is precipitated from the compound of formula (4) generated, is preferable. For example, in the present invention, a temperature from −78° C. to 50° C. is preferable, and a temperature from approximately −10° C. to 20° C. is more preferable. The present reaction can be carried out under normal atmospheric pressure, and it is not particularly necessary to carry out the reaction in a nitrogen atmosphere. However, as necessary, the reaction can also be carried out in an inert gas such as nitrogen, helium or argon, under increased pressure.

The reaction time may be set in a range from 10 minutes to several days. From the viewpoint of reduction of the production costs, the reaction is preferably terminated within 48 hours, and the reaction time is more preferably from 10 minutes to 24 hours.

The compound of formula (4) produced by allowing an acylating agent to act on the compound of formula (3) in the presence of acid is further subjected to crystallization, or to suspension and washing, so that β-anomer can be isolated from the compound of formula (4). In the crystallization operation, a reaction product that contains the compound of formula (4) is suspended in a solvent, and it is then heated to reflux to obtain a solution. Thereafter, the obtained solution is cooled to an ice-cooled temperature, for example, and it is then filtrated to obtain crystals. In the suspension and washing operation, a reaction product that contains the compound of formula (4) is suspended in a solvent, and it is then stirred. Thereafter, the resultant mixture is filtrated to obtain crystals. A solvent used in such crystallization or suspension and washing operation is an alcohol solvent, an ether solvent, water, or a mixture thereof. Preferred alcohol solvents include methanol, ethanol, normal propyl alcohol, isopropyl alcohol, and normal butanol. Preferred ether solvents include diethyl ether, diisopropyl ether, di-normal propyl ether, di-normal butyl ether, methyl isopropyl ether, methyl-t-butyl ether, ethyl-t-butyl ether, tetrahydrofuran, and dioxane.

A method for producing the compound of formula (3) used in the method of the present invention is not particularly limited. For example, a compound represented by the following formula (1):

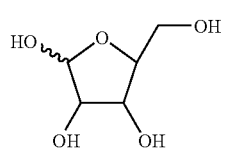

(1)

is allowed to react with lower alcohol in the presence of acid to obtain a compound represented by the following formula (2):

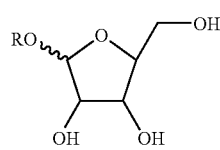

(2)

wherein R represents a lower alkyl group.

Subsequently, a compound represented by X—Cl or $X_2O$ (wherein X represents a protecting group of a hydroxyl group) is allowed to act on the thus produced compound of formula (2), so as to produce the compound of formula (3).

The acid used in the aforementioned reaction may be either weak acid or strong acid. Strong acid is preferable. Moreover, the acid may be either inorganic acid (for example, sulfuric acid, hydrochloric acid, nitric acid, etc.) or organic acid (formic acid, benzoic acid, methanesulfonic acid, trifluoromethanesulfonic acid, p-toluenesulfonic acid, etc.). Inorganic acid is preferable. As such acid, sulfuric acid or hydrochloric acid is particularly preferably used.

The amount of acid used in the aforementioned reaction is 0.001 equivalent to 10 equivalents with respect to the compound of formula (1). From the viewpoint of the reaction time, it is preferably 0.01 equivalent to 5 equivalents, and more preferably 0.05 equivalents to 1 equivalent.

Lower alcohol corresponding to the lower alkyl group represented by R in the above formula (2) can be used in the aforementioned reaction. A specific example is alcohol having a linear, branched or cyclic alkyl group containing 1 to 10 carbon atoms. Examples of lower alcohol include methanol, ethanol, isopropyl alcohol, normal propyl alcohol, normal butyl alcohol, t-butyl alcohol, and cyclohexyl alcohol. Of these, methanol is most preferable.

The amount of lower alcohol used may be 1 time to 100 times, preferably 1 time to 50 times, and more preferably 1 time to 20 times, with respect to the amount of the compound of formula (1).

As a reaction of synthesizing the compound of formula (2), for example, the compound of formula (1) and lower alcohol are added to a vessel such as a flask, and thereafter, acid (for example, sulfuric acid) is slowly added dropwise thereto to carry out the reaction. The reaction temperature is not particularly limited, as long as the reaction progresses at the temperature. The reaction may be carried out at a temperature from approximately 0° C. to 50° C. The reaction may also be carried out at room temperature. The reaction time may be set in a range from 10 minutes to several days. From the viewpoint of reduction of the production costs, the reaction is preferably terminated within 24 hours, and the reaction time is more preferably from 10 minutes to 12 hours.

Subsequently, a compound represented by X—Cl or $X_2O$ (wherein X represents a protecting group of a hydroxyl group) is allowed to act on the thus produced compound of formula (2), so as to produce the compound of formula (3).

As the compound represented by X—Cl or $X_2O$ (wherein X represents a protecting group of a hydroxyl group), there can be used compounds in which X represents a protecting group of a hydroxyl group as described above in the present specification. Particularly preferred specific examples of the compound represented by X—Cl or $X_2O$ (wherein X represents a protecting group of a hydroxyl group) include benzoyl chloride and acetic anhydride.

The amount of the compound represented by X—Cl or $X_2O$ (wherein X represents a protecting group of a hydroxyl group) used may be 1 equivalent or more, preferably 10 equivalents or less, and more preferably 5 equivalents or less, with respect to a single hydroxyl group of the compound of formula (2).

As a reaction of synthesizing the compound of formula (3), when X represents a benzoyl group for example, the compound of formula (2), a solvent (for example, toluene, water, or the like), a base (for example, sodium hydroxide or the like), and a phase-transfer catalyst (for example, tetra-normal-butyl ammonium bromide or the like) are added to a vessel. The mixture is cooled to an ice-cooled temperature, and thereafter, the compound represented by X—Cl or $X_2O$ (wherein X represents a protecting group of a hydroxyl group) (for example, benzoyl chloride or the like) is slowly added dropwise thereto. Thereafter, the temperature is increased, and the reaction can be carried out. The reaction temperature is not particularly limited, as long as the reaction progresses at the temperature. The reaction may be carried out at a temperature from approximately 0° C. to 50° C. The reaction may also be carried out at room temperature. The reaction time may be set in a range from 10 minutes to several days. From the viewpoint of reduction of the production costs, the reaction is preferably terminated within 24 hours, and the reaction time is more preferably from 10 minutes to 12 hours.

As a reaction of synthesizing the compound of formula (3), when X is an acetyl group for example, the compound of formula (2), a solvent (for example, acetic acid, toluene or the like), and a base (for example, pyridine, sodium acetate, sodium carbonate or the like) are added to a vessel. Thereafter, the compound represented by X—Cl or $X_2O$ (wherein X represents a protecting group of a hydroxyl group) (for example, acetic anhydride or the like) is added thereto at a temperature from approximately an ice-cooled temperature to 50° C., and the temperature is then increased, so as to carry out the reaction. This time, a base such as pyridine may be used as a solvent. The reaction temperature is not particularly limited, as long as the reaction progresses at the temperature. The reaction may be carried out at a temperature from approximately 0° C. to 100° C. The reaction may also be carried out at room temperature. The reaction time may be set in a range from 10 minutes to several days. From the viewpoint of reduction of the production costs, the reaction is preferably terminated within 24 hours, and the reaction time is more preferably from 10 minutes to 12 hours.

Various types of derivatives can be produced from the compound of formula (4) produced by the method of the present invention by converting the group at 1-position represented by —OZ of the aforementioned compound to another group.

For example, a nucleic acid derivative obtained by condensing the β-anomer of 1-O-acetyl-2,3,5-tri-O-acyl-ribofuranose obtained by the method of the present invention and a specific nitrogen-containing heterocyclic compound has been known as a physiologically active substance exhibiting antiviral action. For example, 1-(2,3,5-tri-O-acetyl-β-L-ribofuranosyl)-1,2,4-triazole-3-carboxamide that is a nucleic acid derivative induced from a condensation product of 1,2,3,5-tetra-O-acetyl-β-L-ribofuranose and methyl 1,2,4-triazole-3-carboxylate is called L-Ribavirin or Levovirin, which has been known as an antiviral agent. This compound can be produced by the following method (see Patent Document 2 and Non-Patent Documents 1, 2 and 6).

Methyl 1,2,4-triazole-3-carboxylate and 1,2,3,5-tetra-O-acetyl-β-L-ribofuranose are heated under reduced pressure in the presence of trifluoromethanesulfonic acid or bis(p-nitrophenyl)-phosphate. The residue is recrystallized from ethanol or methanol to obtain methyl 1-(2,3,5-tri-O-acetyl-β-L-ribofuranosyl)-1,2,4-triazole-3-carboxylate. Subsequently, the obtained methyl 1-(2,3,5-tri-O-acetyl-β-L-ribofuranosyl)-1,2,4-triazole-3-carboxylate is treated with ammonia in a methanol solvent, and the resultant mixture is then recrystallized from ethanol to obtain a crude product of 1-(2,3,5-tri-O-acetyl-β-L-ribofuranosyl)-1,2,4-triazole-3-carboxamide. The obtained compound is further recrystallized from an ethanol aqueous solution, so as to obtain high-purity 1-(2,3,5-tri-O-acetyl-β-L-ribofuranosyl)-1,2,4-triazole-3-carboxamide.

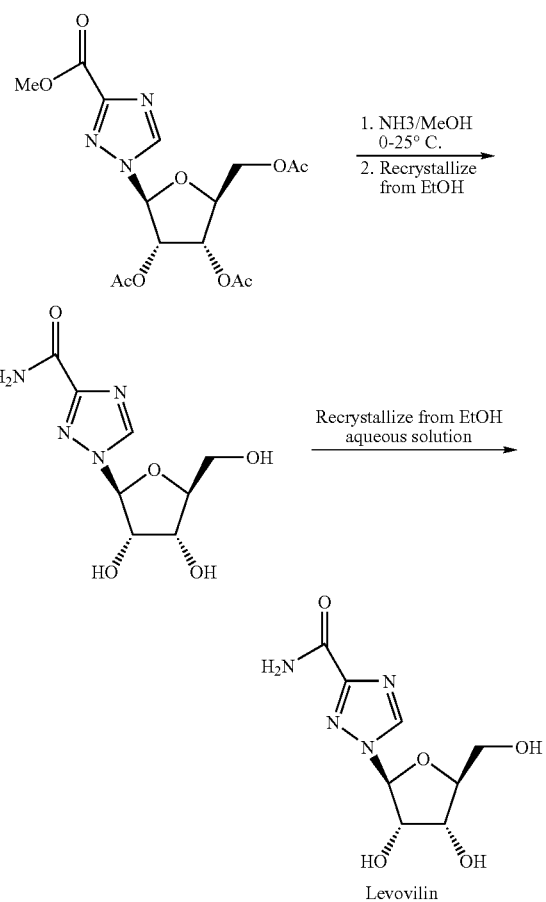

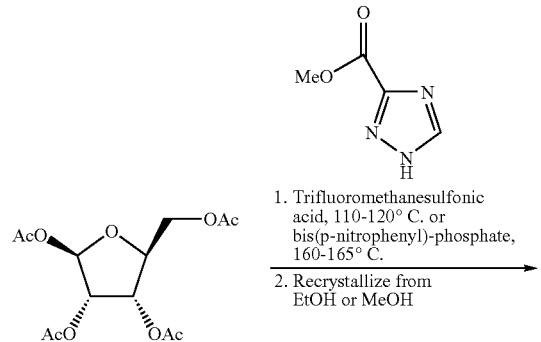

Moreover, for example, 1-O-acetyl-2,3,5-tri-O-benzoyl-β-L-ribofuranose is converted to 3,5-di-O-benzoyl-1-bromo-2-deoxy-2-fluoro-β-arabinofuranose via 4 steps according to the production method described in JP Patent Publication (Kohyo) No. 9-508394 A (1997). The obtained compound is further subjected to condensation with thymine and induction, so as to convert it to Clevudine useful as an antiviral agent. Thus, this is a compound useful as a medical/agrichemical intermediate.

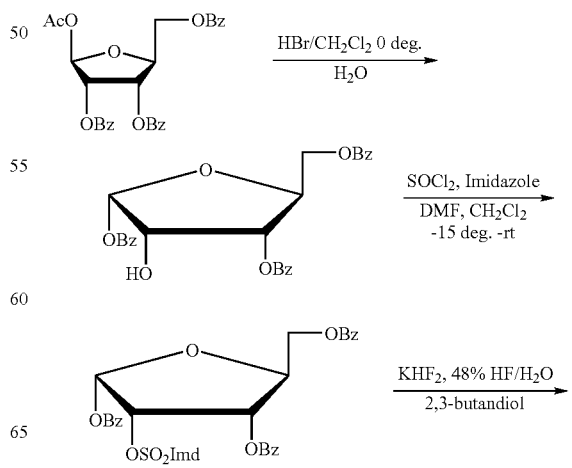

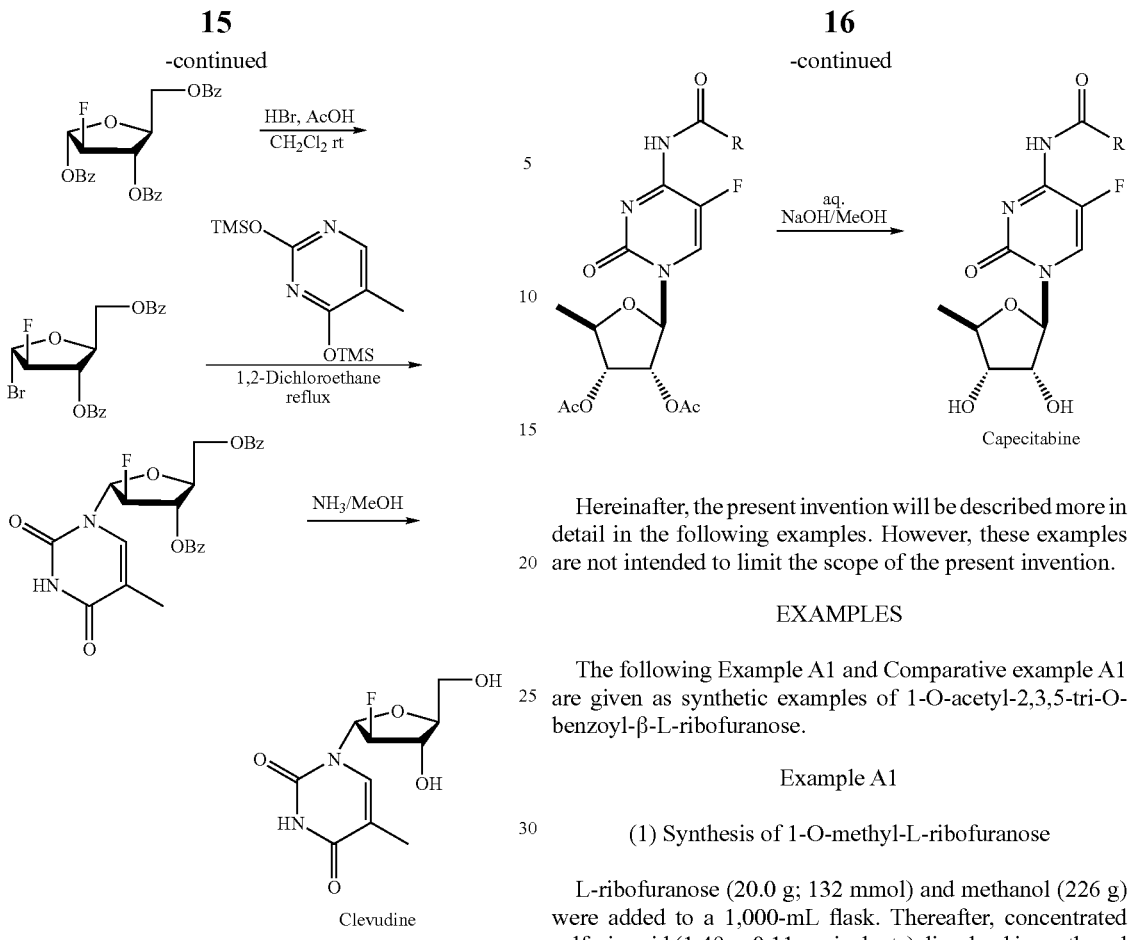

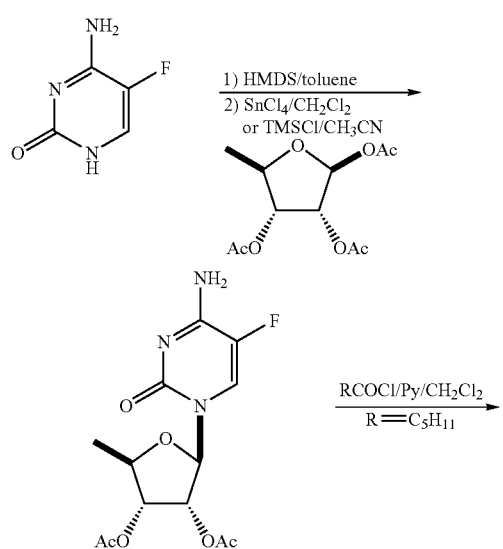

Clevudine

Furthermore, for example, 1,2,3-tri-O-acetyl-5-deoxy-β-D-ribofuranose is subjected to condensation with 5′-fluorocytosine and induction using HMDS according to the production method described in Bioorganic & Medicinal Chemistry, 1697 (2000), etc., so that it can be converted to Capecitabine useful as an anticancer agent. Thus, this is a compound useful as a medical/agrichemical intermediate.

Hereinafter, the present invention will be described more in detail in the following examples. However, these examples are not intended to limit the scope of the present invention.

EXAMPLES

The following Example A1 and Comparative example A1 are given as synthetic examples of 1-O-acetyl-2,3,5-tri-O-benzoyl-β-L-ribofuranose.

Example A1

(1) Synthesis of 1-O-methyl-L-ribofuranose

L-ribofuranose (20.0 g; 132 mmol) and methanol (226 g) were added to a 1,000-mL flask. Thereafter, concentrated sulfuric acid (1.49 g; 0.11 equivalents) dissolved in methanol (21.2 g) was slowly added dropwise thereto. The obtained mixture was reacted at room temperature for 5 hours. Thereafter, sodium acetate (2.40 g) was added to the reaction product for neutralization, and it was then concentrated under reduced pressure, so as to obtain 31.18 g of crude 1-O-methyl-L-ribofuranose as a whitish oily substance.

$^1$H-NMR (400 MHz, D$_2$O-d): δ(β-anomer) 3.38 (s, 3H), 3.57-3.62 (m, 1H), 3.76-3.80 (m, 1H), 3.99-4.03 (m, 2H), 4.13-4.16 (m, 1H), 4.89 (d, J=1.0 Hz, 1H) (α-anomer) 3.42 (s, 3H), 3.63-3.75 (m, 2H), 3.98-4.11 (m, 3H), 4.98 (d, J=4.5 Hz, 1H)

(2) Synthesis of 2,3,5-tri-O-benzoyl-1-O-methyl-L-ribofuranose 31.18 g of the crude 1-O-methyl-L-ribofuranose synthesized in (1) above, toluene (175 ml), a 25 wt. % sodium hydroxide aqueous solution (111 ml), and tetra-normal-butyl ammonium bromide (1.20 g; 5 molar % ratio) were added to a 1-L flask. The obtained mixture was cooled to an ice-cooled temperature, and benzoyl chloride (56.6 mol; 3.05 equivalents) was then slowly added dropwise thereto. The temperature was increased to room temperature, and the reaction was then carried out for 2 hours. The reaction product was again cooled to an ice-cooled temperature, and it was then diluted with toluene (200 ml) and a 1 N sodium hydroxide aqueous solution (100 ml). The temperature was increased to room temperature, and an organic layer was separated from an aqueous layer. The organic layer was washed with a 1 N sodium hydroxide aqueous solution (100 ml) 2 times, and was then washed with a 3 N hydrochloric acid aqueous solution (200 ml), so that the organic layer was concentrated. Thus, 62.69 g of crude 2,3,5-tri-O-benzoyl-1-O-methyl-L-ribofuranose was obtained in the form of a colorless oily liquid.

$^1$H-NMR (400 MHz, CDCl$_3$-d): δ(β-anomer) 3.44 (s, 3H), 4.53-4.58 (m, 1H), 5.72-4.76 (m, 2H), 5.19 (s, 1H), 5.69-5.71 (m, 1H), 5.73-5.76 (m, 1H), 7.32-7.62 (m, 9H), 7.90-8.11 (m, 6H) (α-anomer) 3.65 (s, 3H), 4.53-4.76 (m, 3H), 5.34-5.47 (m, 2H), 5.73-5.76 (s, 1H), 7.32-7.72 (m, 9H), 7.89-7.95 (m, 2H), 8.18-8.21 (m, 4H)

(3) Synthesis of 1-O-acetyl-2,3,5-tri-O-benzoyl-β-L-ribofuranose 59.40 g out of 62.69 g of the crude 2,3,5-tri-O-benzoyl-1-O-methyl-L-ribofuranose synthesized in (2) above was added to a 1-L flask. Thereafter, acetic anhydride (31.2 ml; 2.65 equivalents), acetic acid (26.7 ml; 3.73 equivalents), and pyridine (7.1 ml; 0.8 equivalents) were added to the flask. The obtained mixture was cooled to an ice-cooled temperature, and thereafter, concentrated sulfuric acid (13.5 ml; 2.03 equivalents) was slowly added dropwise thereto. After completion of the reaction for 30 minutes, cold water (200 ml) was slowly added dropwise to the reaction product, and crystals were then filtrated. The obtained solid was dried. Thus, 69.83 g of crude 1-O-acetyl-2,3,5-tri-O-benzoyl-L-ribofuranose was obtained in the form of a light yellow solid. The obtained compound was analyzed by HPLC. As a result, the ratio of α-/β-anomers in the 1-O-acetyl-2,3,5-tri-O-benzoyl-L-ribofuranose was 4/96, and the reaction yield of the β-anomer from the total 3 steps was 84%. 69.83 g of the crude 1-O-acetyl-2,3,5-tri-O-benzoyl-L-ribofuranose was suspended in isopropyl alcohol (92 ml), and the suspension was then heated to reflux for 1 hour. Thereafter, the reaction solution, in which the aforementioned compound had been completely dissolved, was cooled to an ice-cooled temperature, and it was then stirred for 30 minutes. Thereafter, the resultant mixture was filtrated, and the obtained crystals were then dried under reduced pressure. Thus, 1-O-acetyl-2,3,5-tri-O-benzoyl-β-L-ribofuranose was obtained from L-ribofuranose in the form of white crystals with a purity of 99% or more at a total yield of 75%.

$^1$H-NMR (400 MHz, CDCl$_3$-d): δ (β-anomer) 2.00 (s, 3H), 4.51-4.52 (m, 1H), 4.76-4.80 (m, 2H), 5.78-5.79 (m, 1H), 5.89-5.92 (m, 1H), 6.43 (s, 1H), 7.32-7.59 (m, 9H), 7.88-8.07 (m, 6H)

Comparative Example A1

Synthesis of 1-O-acetyl-2,3,5-tri-O-benzoyl-β-L-ribofuranose 5.37 g of crude 2,3,5-tri-O-benzoyl-1-O-methyl-L-ribofuranose synthesized from L-ribose (1.0 g; 6.66 mmol) in accordance with the method described in Helvetica Chimica Acta 1959, (121), 1171-1173p was added to a 100-ml flask. Thereafter, acetic anhydride (3.73 ml; 5.95 equivalents) and acetic acid (1.60 ml; 2.80 equivalents) were added thereto. The obtained mixture was cooled on ice, and thereafter, concentrated sulfuric acid (530 μl; 1.5 equivalents) was slowly added dropwise thereto. After completion of the reaction for 30 minutes, cold water (50 ml) was slowly added dropwise to the reaction solution, and an upper aqueous layer was separated. The precipitated semi-oily solid was dried under reduced pressure. Thus, 3.97 g of crude 1-O-acetyl-2,3,5-tri-O-benzoyl-L-ribofuranose was obtained in the form of a light yellow oily solid. The obtained solid was analyzed by HPLC. As a result, the ratio of α-/β-anomers in the crude 1-O-acetyl-2,3,5-tri-O-benzoyl-L-ribofuranose was 35/65, and the reaction yield of the β-anomer from the total 3 steps was 56%.

$^1$H-NMR (400 MHz, CDCl$_3$-d): δ (β-anomer) 2.00 (s, 3H), 4.51-4.52 (m, 1H), 4.76-4.80 (m, 2H), 5.78-5.79 (m, 1H), 5.89-5.92 (m, 1H), 6.43 (s, 1H), 7.32-7.59 (m, 9H), 7.88-8.07 (m, 6H)

The following Examples B1, B2 and B3, and Comparative examples B1 and B2 are all synthetic examples of 1,2,3,5-tetra-O-acetyl-β-L-ribofuranose.

Example B1

(1) Synthesis of 2,3,5-tri-O-acetyl-1-O-methyl-L-ribofuranose

A 500-ml four-necked flask was subjected to nitrogen substitution. Thereafter, 60.0 g (400 mmol) of L-ribose and 300 ml of methanol were added to the flask, and they were then cooled to 5° C. under ice bath cooling. Thereafter, 5.60 g of concentrated sulfuric acid was added to the resultant mixture. Subsequently, the temperature of the mixture was increased to room temperature, followed by stirring for 4 hours. Thereafter, 14.7 g of sodium acetate was added to the reaction solution, and the obtained mixture was then stirred for 30 minutes. Methanol was distilled away from the reaction mixture under reduced pressure, and 120 ml of acetic acid was then added thereto and was subjected to reduced-pressure distillation. It was confirmed by NMR that no methanol remained, and that 1.7 equivalents of acetic acid remained with respect to the ribose derivative. The reaction product was directly subjected to the subsequent process.

119 g of acetic acid and 151 g of acetic anhydride were added to the obtained reaction mixture, so that the amount of the acetic acid became 5 equivalents with respect to the amount of the ribose derivative. The temperature was increased to 100° C., and the mixture was then stirred for 4 hours. Thereafter, the temperature was cooled to room temperature, and 150 ml of toluene was then added to the reaction product, concentrated under reduced pressure. 100 ml of toluene was added to the residue, followed by concentration. This operation was repeated 2 times. To the thus obtained residue, 165 ml of ethyl acetate and 150 ml of water were added, and the reaction mixture was then neutralized by addition of sodium bicarbonate, followed by liquid separation. The organic layer was washed with 150 ml of a saturated sodium chloride aqueous solution, and it was then dried with anhydrous sodium sulfate. The drying agent was removed by filtration, and the residue was then concentrated under reduced pressure to obtain 113.2 g of yellow syrup. This syrup was defined as a crude product of 2,3,5-tri-O-acetyl-1-O-methyl-L-ribofuranose, and it was then subjected to the subsequent process without purification.

(2) Synthesis of 1,2,3,5-tetra-O-acetyl-β-L-ribofuranose

A 200-ml four-necked flask was subjected to nitrogen substitution. 11.32 g (corresponding to 40 mmol L-ribose) of the 2,3,5-tri-O-acetyl-1-O-methyl-L-ribofuranose obtained in Example B1(1) and 40 ml of diisopropyl ether were added to the flask. The mixture was maintained at a temperature of 0±5° C. or lower in an ice bath, and 8.17 g (2.0 equivalents) of acetic anhydride, 4.80 g (2.0 equivalents) of acetic acid, and 2.53 g (0.8 equivalents) of pyridine were then added thereto. While stirring in an ice bath, 8.8 g (2.2 equivalents) of concentrated sulfuric acid was added dropwise to the reaction solution at an internal temperature of 0±5° C. or lower. The obtained mixture was stirred in an ice bath for 3.5 hours, and the reaction product was then maintained at 5° C. or lower in a refrigerator overnight. While stirring in an ice bath, 21.65 g of sodium acetate was added to the reaction product, and the obtained mixture was then stirred in an ice bath for 30 minutes. 120 ml of ethyl acetate and a saturated sodium bicarbonate aqueous solution were added to the reaction solution at room temperature until the aqueous layer was neutralized, followed by liquid separation. The aqueous layer was extracted with 120 ml of ethyl acetate, and organic layers were gathered. The gathered layers were washed with 120 ml of a saturated sodium bicarbonate aqueous solution and then with 120 ml of a saturated sodium chloride aqueous solution 2 times. The organic layer was dried over anhydrous sodium sulfate, and the drying agent was then removed by filtration, concentrated under reduced pressure. Thus, 14.23 g of crude 1,2,3,5-tetra-O-acetyl-L-ribofuranose was obtained in the form of yellow oil. The obtained compound was analyzed by HPLC. As a result, it was found that the crude product contained 10.13 g of 1,2,3,5-tetra-O-acetyl-L-ribofuranose, that the ratio of α-/β-anomers was 7/93, and that the total reaction yield of the β-anomer from L-ribose was 74%. By crystallization from 14.23 g of the crude 1,2,3,5-tetra-O-acetyl-L-ribofuranose using ethanol, 8.86 g of 1,2,3,5-tetra-O-acetyl-β-L-ribofuranose was obtained in the form of white crystals at a total yield of 70% from L-ribose.

$^1$H-NMR (400 MHz, CDCl$_3$, TMS=0 ppm): δ (β-anomer) 2.08 (s, 3H), 2.09 (s, 3H), 2.10 (s, 3H), 2.13 (s, 3H), 4.12-4.19 (m, 1H), 4.30-4.40 (m, 2H), 5.32-5.38 (m, 2H), 6.17 (s, 1H) ppm Example B2

Synthesis of 1,2,3,5-tetra-O-acetyl-β-L-ribofuranose

A 100-ml four-necked flask was subjected to nitrogen substitution. 11.32 g (corresponding to 40 mmol of L-ribose) of the 2,3,5-tri-O-acetyl-1-O-methyl-L-ribofuranose obtained in Example B1(1) and 20 ml of diisopropyl ether were added to the flask. The flask was maintained at a temperature of 0±5° C. in an ice bath, and 8.17 g (2.0 equivalents) of acetic anhydride was added thereto. While stirring in an ice bath, 3.2 g (0.8 equivalents) of concentrated sulfuric acid was added dropwise thereto at an internal temperature of 0±5° C. The mixture was stirred in an ice bath for 3.5 hours, and the reaction product was then maintained at 5° C. or lower in a refrigerator overnight. While stirring in an ice bath, 7.87 g of sodium acetate was added to the reaction product, and the obtained mixture was then stirred in an ice bath for 30 minutes. 120 ml of ethyl acetate and a saturated sodium bicarbonate aqueous solution were added to the reaction solution at room temperature until the aqueous layer was neutralized, followed by liquid separation. The aqueous layer was extracted with 120 ml of ethyl acetate, and organic layers were gathered. The gathered layers were washed with 120 ml of a saturated sodium bicarbonate aqueous solution and then with 120 ml of a saturated sodium chloride aqueous solution 2 times. The organic layer was dried over anhydrous sodium sulfate, and the drying agent was then removed by filtration, concentrated under reduced pressure. Thus, 16.10 g of crude 1,2,3,5-tetra-O-acetyl-L-ribofuranose was obtained in the form of yellow oil. The obtained compound was analyzed by HPLC. As a result, it was found that the crude product contained 9.76 g of 1,2,3,5-tetra-O-acetyl-L-ribofuranose, that the ratio of α-/β-anomers was 7/93, and that the total reaction yield of the β-anomer from L-ribose was 72%.

Example B3

Synthesis of 1,2,3,5-tetra-O-acetyl-β-L-ribofuranose

A 100-ml four-necked flask was subjected to nitrogen substitution. 2.97 g (purity: 98 wt %; corresponding to 10 mmol of L-ribose) of the 2,3,5-tri-O-acetyl-1-O-methyl-L-ribofuranose obtained at a yield of 93.5% from L-ribose was added to the flask by the same method as that of Example B1(1). Thereafter, 1.85 ml (2.0 equivalents) of acetic anhydride, 1.14 ml (2.0 equivalents) of acetic acid, and 0.64 ml (0.8 equivalents) of pyridine were added thereto. While stirring in an ice bath, 2.2 g (2.2 equivalents) of concentrated sulfuric acid was added dropwise thereto at an internal temperature of 0±5° C. The temperature was increased to room temperature, and the reaction solution was stirred for 1.5 hours. Thereafter, the reaction solution was maintained at a temperature of 0±5° C. again in an ice bath, and 10 ml of diisopropyl ether was added thereto, followed by stirring in an ice bath for 4 hours. Thereafter, the reaction product was maintained at 5° C. or lower in a refrigerator overnight. While stirring in an ice bath, 3.60 g of sodium acetate was added to the reaction product, and the obtained mixture was then stirred in an ice bath for 30 minutes. 30 ml of ethyl acetate and a saturated sodium bicarbonate aqueous solution were added to the reaction solution at room temperature until the aqueous layer was neutralized, followed by liquid separation. The aqueous layer was extracted with 30 ml of ethyl acetate, and organic layers were then gathered. The gathered layers were washed with 20 ml of a saturated sodium bicarbonate aqueous solution and then with 20 ml of a saturated sodium chloride aqueous solution 2 times. The organic layer was dried over anhydrous sodium sulfate, and the drying agent was then removed by filtration, concentrated under reduced pressure. Thus, 3.67 g of crude 1,2,3,5-tetra-O-acetyl-L-ribofuranose was obtained in the form of yellow oil. The obtained compound was analyzed by HPLC. As a result, it was found that the crude product contained 2.63 g of 1,2,3,5-tetra-O-acetyl-L-ribofuranose, that the ratio of α-/β-anomers was 6/94, and that the total reaction yield of the β-anomer from L-ribose was 73%.

Comparative Example B1

Synthesis of 1,2,3,5-tetra-O-acetyl-β-L-ribofuranose

The same operations as those of Example B1 were carried out with the exception that the half-scale (corresponding to 20 mmol of L-ribose) was used and that diisopropyl ether was not added. As a result, 5.60 g of crude 1,2,3,5-tetra-O-acetyl-L-ribofuranose was obtained in the form of yellow oil. The obtained compound was analyzed by HPLC. As a result, it was found that the crude product contained 3.98 g of 1,2,3,5-tetra-O-acetyl-L-ribofuranose, that the ratio of α-/β-anomers was 21/79, and that the total reaction yield of the β-anomer from L-ribose was 49%.

Comparative Example B2

Synthesis of 1,2,3,5-tetra-O-acetyl-β-L-ribofuranose

The same operations as those of Example B2 were carried out with the exception that the half-scale (corresponding to 20 mmol of L-ribose) was used and that diisopropyl ether was not added. As a result, 5.82 g of crude 1,2,3,5-tetra-O-acetyl-L-ribofuranose was obtained in the form of yellow oil. The obtained compound was analyzed by HPLC. As a result, it was found that the crude product contained 2.82 g of 1,2,3,5-tetra-O-acetyl-L-ribofuranose, that the ratio of α/β-anomers was 19/81, and that the total reaction yield of the β-anomer from L-ribose was 36%.

The invention claimed is:

1. A method for producing a compound represented by the following formula (4):

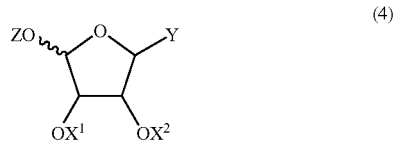

wherein each of $X^1$ and $X^2$ represents a protecting group of a hydroxyl group, which may be the same or different, Y represents $CH_2OX^3$ or $CH_3$; $X^3$ represents a protecting group of a hydroxyl group; and Z represents an acyl group, which comprises allowing an acylating agent to react with a compound represented by the following formula (3) in the presence of acid:

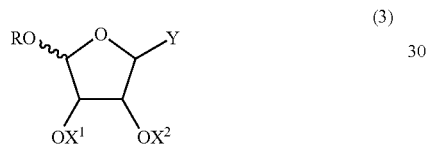

wherein each of $X^1$ and $X^2$ represents a protecting group of a hydroxyl group, which may be the same or different; Y represents $CH_2OX^3$ or $CH_3$; $X^3$ represents a protecting group of a hydroxyl group; and R represents a lower alkyl group, wherein 6 equivalents or less of the acylating agent, with respect to the amount of the compound of formula (3) used, is allowed to react with the compound of the formula (3), and/or the acylating agent is allowed to react with the compound of the formula (3) in the presence of a poor solvent, so that the produced compound represented by formula (4) whose configuration at 1-position is β (β-anomer) is precipitated.

2. The method according to claim 1, wherein the ratio of the α-anomer/β-anomer (α-anomer:β-anomer) as to the configuration at 1-position of the generated compound of formula (4) is 30:70 to 0:100.

3. The method according to claim 1, wherein the acid is a strong acid.

4. The method according to claim 1, wherein the acid is sulfuric acid.

5. The method according to claim 1, wherein the amount of the acid used is 5 equivalents or less with respect to the amount of the compound of formula (3) used.

6. The method according to claim 1, which further comprises adding a base.

7. The method according to claim 6, wherein the amount of the acid used is 3 equivalents or less with respect to the amount of the compound of formula (3) used.

8. The method according to claim 6, wherein the base is pyridine.

9. The method according to claim 1, wherein the acylating agent is acetic acid, acetic anhydride, or a mixture thereof.

10. The method according to claim 9, wherein the amount of the acetic anhydride used is 3 equivalents or less with respect to the amount of the compound of formula (3) used, or the amount of the acetic acid used is 5 equivalents or less with respect to the amount of the compound of formula (3) used.

11. The method according to claim 1, wherein the poor solvent is any one of an ether solvent, an aliphatic hydrocarbon solvent, and an aromatic hydrocarbon solvent.

12. The method according to claim 11, wherein the amount of any one of the ether solvent, the aliphatic hydrocarbon solvent, and the aromatic hydrocarbon solvent is 20 times or less with respect to the amount of the compound of formula (3).

13. The method according to claim 1, wherein the compound of formula (3) is used, which is obtained by allowing a compound represented by the following formula (1) to react with a lower alcohol in the presence of acid:

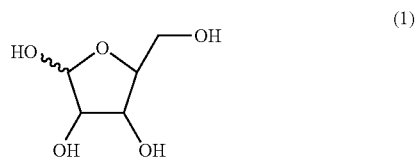

so as to produce a compound represented by the following formula (2):

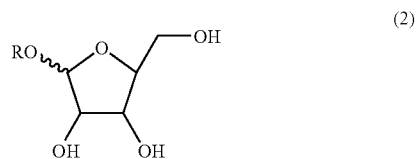

wherein R represents a lower alkyl group, and then allowing a compound represented by X—Cl or $X_2O$ wherein X represents a protecting group of a hydroxyl group, to act on the thus produced compound of formula (2) to obtain the compound of formula (3).

14. The method according to claim 1, which comprises isolating the β-anomer of the produced compound of formula (4) by further crystallizing the compound of formula (4) by further subjecting the compound of formula (4) to crystallization or to suspension and washing.

15. The method according to claim 14, wherein the solvent used in the crystallization or the suspension and washing is an alcohol solvent, an ether solvent, water, or a mixture thereof.

16. The method according to claim 1, which further comprises condensing the product compound of formula (4) to a nitrogen-containing heterocyclic compound, a thymine, or a 5'-fluorocytosine.

* * * * *